(12) United States Patent
Di Santo

(10) Patent No.: US 9,775,995 B2
(45) Date of Patent: Oct. 3, 2017

(54) TREATING SKIN ULCERS

(71) Applicant: BODYFLOW INTERNATIONAL PTY LTD, Port Melbourne, Victoria (AU)

(72) Inventor: Joe Di Santo, Blackburn North (AU)

(73) Assignee: BODYFLOW INTERNATIONAL PTY LTD ACN, Caulfield North, Victoria (AU)

( * ) Notice: Subject to any disclaimer, the term of this patent is extended or adjusted under 35 U.S.C. 154(b) by 0 days.

(21) Appl. No.: 14/894,552

(22) PCT Filed: Jun. 13, 2014

(86) PCT No.: PCT/AU2014/000620
§ 371 (c)(1),
(2) Date: Nov. 30, 2015

(87) PCT Pub. No.: WO2014/201493
PCT Pub. Date: Dec. 24, 2014

(65) Prior Publication Data
US 2016/0136417 A1 May 19, 2016

(30) Foreign Application Priority Data
Jun. 21, 2013 (AU) .................. 2013902267

(51) Int. Cl.
*A61N 1/32* (2006.01)
*A61N 1/04* (2006.01)
(Continued)

(52) U.S. Cl.
CPC .......... *A61N 1/326* (2013.01); *A61N 1/0468* (2013.01); *A61N 1/205* (2013.01); *A61N 1/328* (2013.01); *A61N 1/36014* (2013.01)

(58) Field of Classification Search
CPC ........ A61N 1/32; A61N 1/3606; A61N 1/205; A61N 1/18; A61N 1/36; A61N 1/0468;
(Continued)

(56) References Cited

U.S. PATENT DOCUMENTS

| 5,158,081 A | 10/1992 | McWhorter et al. |
| 6,745,078 B1 * | 6/2004 | Buchner ................ A61N 1/326 607/72 |

(Continued)

FOREIGN PATENT DOCUMENTS

| AU | WO2013071332 A1 | 5/2013 |
| CA | 2620288 A1 | 8/2009 |

(Continued)

OTHER PUBLICATIONS

Australian Patent Office, International Search Report of the International Searching Authority on PCT/AU2014/000620, dated Sep. 15, 2014, PO Box 200, Woden Act 2606, Australia.

*Primary Examiner* — Deborah Malamud
(74) *Attorney, Agent, or Firm* — Louis Ventre, Jr.

(57) ABSTRACT

The invention provides the use of electrical pulses (I, W) to reduce, improve, heal or prevent recurrence of a chronic ulcer, comprising administering to a need (1, 2, 3) an effective amount of an electric stimulation in multiple treatment sessions, wherein the electric stimulation stimulates the lymphatic system.

10 Claims, 3 Drawing Sheets

(51) Int. Cl.
*A61N 1/20* (2006.01)
*A61N 1/36* (2006.01)

(58) Field of Classification Search
CPC ...... A61N 1/328; A61N 1/36175; A61N 1/00; A61N 1/0432; A61N 1/0464; A61B 5/4848; A61B 5/418; A61B 5/445; A61B 5/4836
See application file for complete search history.

(56) References Cited

U.S. PATENT DOCUMENTS

2008/0161884 A1\* 7/2008 Chandler ............. A61N 1/0468
607/50
2012/0041513 A1\* 2/2012 Tucker ............... A61N 1/36003
607/48

FOREIGN PATENT DOCUMENTS

| IL | WO0191697 | A2 | 12/2001 |
| WO | WO03090845 | A2 | 11/2003 |
| WO | WO2006054118 | A1 | 5/2006 |

\* cited by examiner

TREATING SKIN ULCERS

FIELD

The present invention relates to ulcers, particularly to a method for substantially reducing, improving, healing or preventing a recurrence of skin ulcers.

BACKGROUND

Chronic skin ulcers can be a persistent problem resulting from sustained oxygen deprivation of tissue, arising from a variety of root causes. Major causes include (i) mechanical pressure around bony prominences from long periods of bed rest preventing adequate blood flow (pressure sores), and (ii) the failure of non-return valves in the veins resulting in the pooling of blood in the legs when standing (venous leg ulcers).

The standard of care for treatment and prevention of chronic ulcers typically includes mechanical strategies to assist in the passage of blood to the affected tissues. In the case of pressure sores, regular movement of the patient to reduce the sustained pressure is often used, which may be assisted with electrically operated cushion supports that dynamically shift the pressure points. In the case of leg ulcers, elevation of the affected leg assists in drainage of the blood and compression bandages around the wound help to reduce swelling which in turn assists in peripheral blood flow.

Electrical stimulation of the affected area has been investigated for many decades as an aid in the healing of chronic ulcers. Despite many positive studies, electrical stimulation has not become broadly adopted as part of the standard of care, perhaps due to variability of research results and unresolved uncertainty as to the best form of electrical stimulation to apply.

The biological mechanism by which the electrical stimulation may operate to accelerate ulcer healing is uncertain, although early thoughts centred on the role of the "healing current" which has long been known to occur in a healing wound.

In an early study in 1976 Gault et al [Gault 1976] found that low intensity direct current approximately doubled the rate of healing of ischaemic skin ulcers. In 1988, Kloth et al [Kloth 1988] found in a small study of stage IV ulcers that pulsed monophasic high-voltage stimulation (twin peaked pulses, 105 Hz, 100 to 175 V, 45 minutes per day) with the electrodes applied either side of the wound, or over the wound if improvement plateaued, was able to eventually heal all 9 treated ulcers in a mean time of 7.3 weeks. In 1991, Griffin et al [Griffin 1991] in a study of monophasic high-voltage stimulation, pressure sores from 9 patients with spinal cord injury (twin peaked pulses, 100 Hz, 200 V, 1 hour per day, cathode placed over the wound) found that after 20 days reduction in wound area was 80% compared with a control group of 52% reduction. In 1991, Feedar et al [Feedar 1991] in a study of monophasic high current stimulation (132 μs rectangular pulses 29 mA, 64 Hz and 128 Hz) 14 treated ulcers (mainly pressure sores) reduced in size about twice as fast over a four week period as control ulcers (55% reduction versus 30% reduction).

In 1993, Wood et al [Wood 1993] in a multicentre double-blind study of pulsed low intensity direct current (300 μA DC pulsing to 600 μA at a frequency of 0.8 Hz) 43 treated stage II and stage III chronic ulcers reduced in size by an average of 85% over eight weeks compared to a rise in the control groups. Wood et al attributed the apparent higher success rate to reduced (sub milliamp) current on the basis that a current of about 600 μA was believed to be optimal for electrochemical healing parameters measured in animals.

In 1996, Baker et al. [Baker 1996] in a study on pressure sores compared high-voltage pulse stimulation (pulse width 100 to 300 μs, 50 Hertz) with a "sham" control of 4 mA 10 μs pulses at 1 Hz and a control of no stimulation and found that the high-voltage 50 Hz stimulation was more effective than the "sham" control and the zero stimulation control. The authors noted that the "sham" control appeared to have some activity, despite the very short 10 μs pulses, but drew no conclusions from that.

In 2003 Houghton et al [Houghton 2003] in a study on leg ulcers found that high-voltage poles stimulation (pulse width 100 μs's, 100 Hz, 150 V) for 45 minutes three times weekly over four weeks produced an average 44.3% decrease in wound area compared to 16% in sham controls.

From the above-mentioned prior investigations, it appears that the enduring popular treatment modality amongst investigators is high-voltage pulsed stimulation at a frequency between 50 and 100 Hz. Typically, the voltage applied is 100 V or more which would be expected to deliver well over 1 mA of current in most treatment situations. Such frequencies may be expected to stimulate the skeletal muscle, which could assist with mobilisation of blood and lymph flow. However, no satisfactory theory for the efficacy of such frequencies and currents is accepted and indeed the DC current results of Wood et al. described above are as good or better than the high frequency stimulation. DC currents are supposedly effective by virtue of electrochemical changes in the wound brought about by the constant direct current. In the absence of comprehensive double-blind studies directly comparing different methodologies, which among several currents and waveforms is optimum for the treatment of ulcers is unknown.

A massage protocol called manual lymphatic drainage (MLD) has limited efficacy in reducing accumulation of lymph (lymphoedema) and while it is sometimes used as part of the treatment modality for ulcers, MLD is not typically regarded as a major or strongly effective component in ulcer healing.

The background state-of-the-art therefore focuses on either electrochemical stimulation by DC currents or skeletal muscle stimulation by high frequency pulsed current.

The inventor believes that an electrical waveform targeted towards stimulation of the lymphatic system may have enhanced utility in the treatment of chronic ulcers, and that the importance of the lymphatic system has been underestimated in the treatment of ulcers.

SUMMARY OF THE INVENTION

According to a first broad aspect of the invention there is provided a method of reducing, improving, healing or preventing recurrence of a chronic ulcer, the method comprising administering to a patient in need an effective amount of an electric stimulation in multiple treatment sessions, wherein the electric stimulation stimulates the lymphatic system.

In one embodiment, the electrical stimulation has a stimulation time profile comprising short pulses of current having a pulse width substantially shorter than an interval between the pulses. The pulse width may be less than 12 ms, preferably less and 8 ms, more preferably less than 3 ms, and is typically about 2 ms.

In one embodiment, the interval between the pulses is greater than 40 ms and less than 1000 ms, preferably greater than 300 ms and less than 1000 ms, more preferably greater than 400 ms and is less than 700 ms.

In one embodiment, an instantaneous maximum current delivered during the pulses is less than 200 mA, preferably less than 20 mA, more preferably less than 10 mA and greater than 0.5 mA.

In one embodiment, the pulses comprise a first series of multiple pulses of a first polarity interspersed with a second series of multiple pulses of an opposite second polarity.

In one embodiment, there are less than 20 pulses in either of the series of pulses, preferably less than 10.

In one embodiment, most of the treatment sessions comprise a total period of administration of the stimulation of less than two hours and greater than 5 minutes, preferably about 20 minutes.

In one embodiment, there are at least two treatment sessions per week, preferably at least five.

In one embodiment, the treatment sessions so until the ulcer completely heals.

In one embodiment, the treatment sessions are continued after healing of the ulcer so as to prevent recurrence of the ulcer.

In one embodiment, the electrical stimulation includes a DC current component of up to 1 mA.

In one embodiment, the electrical stimulation includes an electrical current with a dominant low-frequency component between 1 Hz and 3 Hz, preferably between 1.5 Hz and 2.5 Hz.

In one embodiment, the ulcer is disposed on a leg of the patient and stimulation is provided through electrodes placed so as to stimulate the lymphatic system proximate the ulcer.

In one embodiment, the ulcer is disposed on a leg of the patient and stimulation is provided through electrodes placed so as to stimulate the lymphatic system along a substantial portion of the leg.

According to a second broad aspect of the invention there is provided electrical pulses, for use in reducing, improving, healing or preventing recurrence of a chronic ulcer in a patient, the pulses being applied through one or more pairs of electrodes contacting a skin surface of the patient in multiple treatment sessions, wherein the electrical pulses stimulate a lymphatic system of the patient.

DETAILED DESCRIPTION OF EMBODIMENTS

An embodiment of the current invention will now be described, with reference to 2 examples of patients treated according to the invention.

In both examples, the device for delivering the electrical stimulation is provided by the Bodyflow® models CX1 and P2Ch, for in-hospital post-operative treatment and post-discharge, self-administered applications, respectively. Both Bodyflow units have been approved for use in Australia by the Therapeutic Goods Association (TGA).

The Bodyflow® units are marketed by Bodyflow International Pty Ltd (Victoria, Australia; www.bodyflowinternational.com). The characteristic electrical pulses produced by these units comprise short non-rectangular pulses in the millisecond range separated by gaps in the second range. These waveforms have previously been shown to reduce lymphoedema inpatients with lymphoedema of the legs [Piller 2010] and have other therapeutic benefits such as improved blood circulation. The Bodyflow CX1 unit can work in two modes, called "Standard", which has a pulse width of 6 ms and a time between pulses of 658 ms (1.52 Hz), and "light", which has a pulse width of 6 ms and a time between pulses of 580 ms (1.72 Hz). The Bodyflow P2Ch unit also can work in two modes, called "Standard", which has a pulse width of 2 ms and a time between pulses of 500 ms (2.0 Hz), and "light", which has a pulse width of 2 ms and a time between pulses of 580 ms (1.72 Hz). Early research on the range of useful pulse widths, frequencies and polarities for an earlier device, and adopted and adapted herein was reported in US Patent application publication number 2006/0064129. Although the Bodyflow units concentrate on stimulation with a dominant low frequency between 1.5 Hz and 2 Hz, the invention extends to any waveform which targets the lymphatic system. Methods of targeting the lymphatic system are far from well established and alternative waveforms may in the future be identified that can be successfully used in the current invention.

Figure 1:
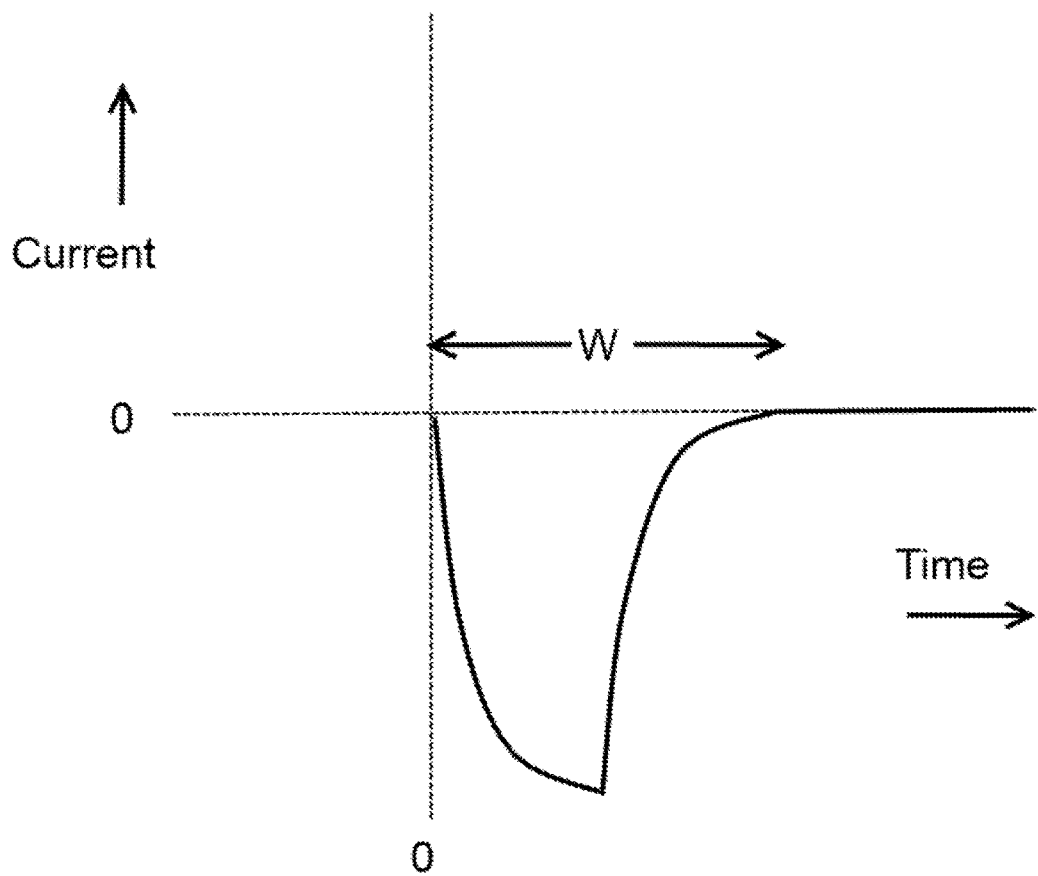
FIG. 1 is a time profile of each pulse used in one embodiment of the invention.
Figure 2:
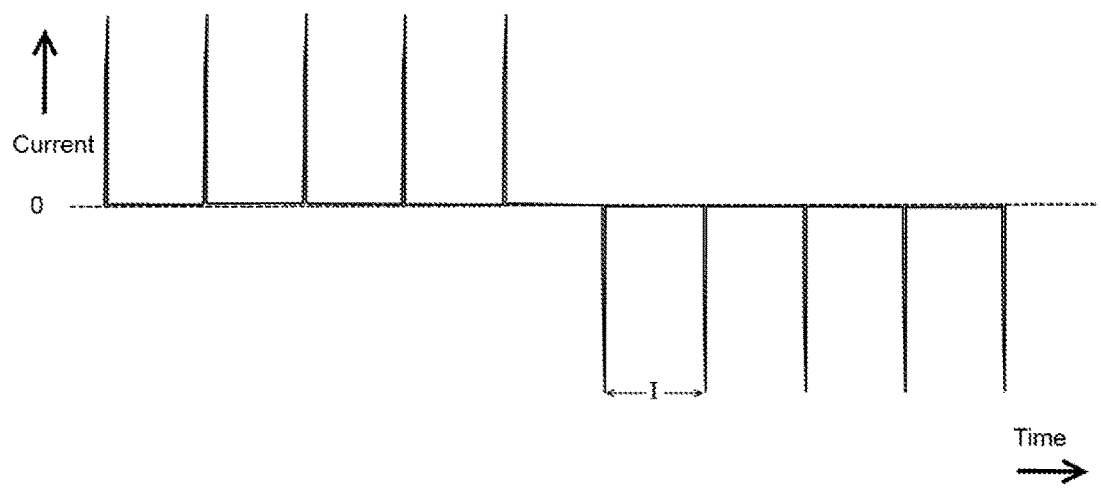
FIG. 2 is a time profile showing series of pulses used in one embodiment of the invention.

Referring now to FIG. 1, the time profile of each pulse in the Bodyflow units is shown, with pulse width W marked. Referring to FIG. 2, an expanded time profile is shown of the pulse train, which appears in interspersed series of pulses with opposite polarities, each pulse separated by an interval I, 5 pulses in each series. The Bodyflow units have an intensity control for the delivered maximum current which is adjustable from a delivered maximum current of 0 mA up to 75 mA. In practice, the appropriate level depends on the nature of the tissue, the distance between the electrodes and the desired effect. Typically, in use, the intensity control is adjusted upwards until there is a slight visible muscular twitch in response to each pulse and either maintained at around this level or slightly below. For the application contemplated here, the maximum current is typically greater than 1 mA and is usually found to be around 5 to 15 mA. Treatment sessions typically last around 20 minutes and may involve one or two pairs of electrodes.

Figure 3:
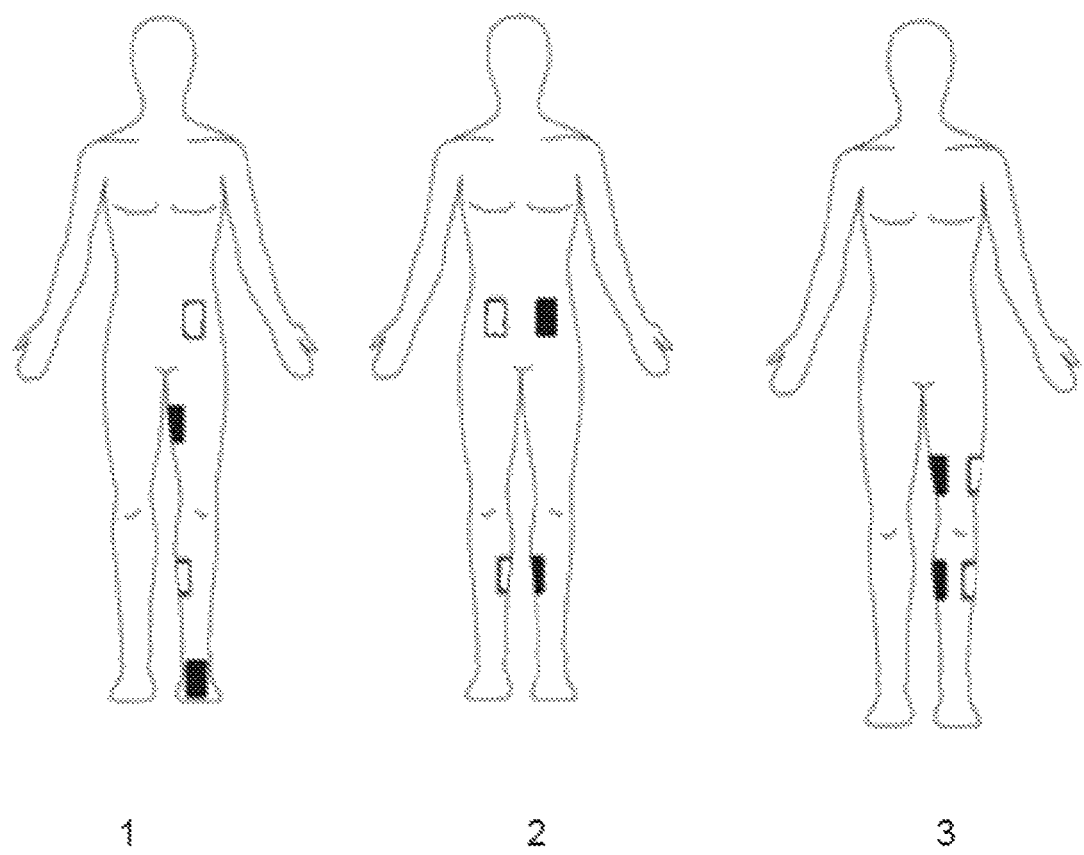
FIG. 3 is a diagram showing alternative placement of electrodes in one embodiment of the invention.

Referring to FIG. 3, placement of the electrodes to optimise stimulation of the lymphatic drainage advantageously stimulates along the length of the lymphatic ducts in the limb concerned, but optimal placement will depend upon the needs of the patient and the areas of the lymphatic system which are compromised. The Bodyflow unit comprises two sets of electrodes, coloured differently, shown in FIG. 3 as white and black. Each set of electrodes corresponds to an independent stimulation channel which can be separately adjusted. Arrangement 1 corresponds to an optimum arrangement for stimulating the lymphatic system of a patient's left leg, with one channel stimulating between the top of the foot and the quadriceps, and another channel stimulating between the inside calf and the torso or groin. Arrangement 2 is appropriate for a stimulation attempting to stimulate both legs at once, and arrangement 3 is an example of stimulating the lymphatic system around one knee.

In the examples that follow the Bodyflow models P2Ch were used, for in-home, self-administered applications, in standard mode. Both Bodyflow units have been approved for use in Australia by the Therapeutic Goods Association (TGA). Electrode placement depends on the particular location of the ulcer, but may not necessarily be directly adjacent to the ulcer, as described above, particularly where the skin is in poor condition.

EXAMPLE 1

This female patient aged 62 years had a venous ulcer accompanied by some lymphoedema in existence for 5 months. The wound size was about 12 cm$^2$ located just above the ankle on the patient's left leg. Prior to treatment, the wound was not progressing well and had remained stagnant for four months. The patient was instructed in the use of the BodyFlow unit, recommended to use four treatment sessions daily of 20 minutes each, and was instructed in the placement of the electrodes. In this case, placement of the electrodes was on the affected limb similar to arrangement 1 in FIG. 3. Tubular compression bandages were also used.

Patient's compliance was adequate, choosing to use the unit twice per day for one hour each session, but missed about one day per week.

After eight weeks of treatment the wound was completely healed and treatment was stopped. Her leg circumference had also reduced substantially in size, probably due to lymphatic drainage and appears much healthier.

EXAMPLE 2

This female patient aged 58 years had two very large round ulcers, one on each leg near the back of her calf, of mixed aetiology, initially 62 cm$^2$ in area on the left leg and 90 cm$^2$ in area on the right leg. These wounds had been in existence for 5-6 years. The trial is still ongoing as of the date of writing. As with the previous example, this patient has been instructed in the use of the unit and recommended to use it for treatment sessions four times daily of 20 minutes each. Electrode placement could not be practically achieved as in arrangement 1 of FIG. 3, instead the lowest connection for each channel was just below the knee, due to the poor condition of the skin in the ischaemic region. No compression bandages were used.

The patient's compliance is average to poor due to fragile emotional state, and she complains of some pain to parts of her legs during the treatments needing to find comfortable electrode placements. On average she misses two or three days per week for varying reasons. On days that she does use the unit, it is twice daily for 45 minutes per session.

The patient is visited every second week to assist her to maintain compliance. Assessment after four weeks showed a definite positive improvements with reduction in lymphoedema and general healthy appearance, as well as reduction in ulcer size. Formal measurements were not made at the four week assessment. Assessment after 20 weeks showed a reduced ulcer size of 15 cm$^2$ on the left leg and 13 cm$^2$ on the right leg, although not healed.

EXAMPLE 3

This patient is an 84-year-old woman having a venous leg ulcer of initial size about 21 cm$^2$ with a suspected arterial component which has been in existence for 3 to 4 years. The patient was instructed in the use of the unit and recommended to use it for treatment sessions twice daily of 20 minutes each. 2-layer Tubigrip compression bandages were also used. After 20 weeks, the wound was not healed and the wound size continued to fluctuate, being measured at 74 cm$^2$ at the 20 week point.

Although many more patients need to be treated to confirm the efficacy of the invention, these results are promising and suggest that the invention may provide an improved efficacy over previously investigated electrical stimulation modalities, at least in some patient groups and particularly where malfunctioning of the lymphatic system is a highly contributory factor.

Persons skilled in the art will appreciate that many variations may be made to the invention without departing from the scope of the invention.

For example, the electrical stimulation of the invention may be augmented with one or several standard care approaches, including but not limited to compression bandages, elevation etc, or augmentation with a DC component of electrical stimulation as previously reported in the literature.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "stimulates the lymphatic system" in the broadest aspect of the invention and the broadest claim encompasses any electrical stimulation modality which has been shown to specifically enhance performance of the lymphatic system, such as for example may be evidenced by reduction of lymphoedema in patients. The term includes electrical stimulation modalities that may stimulate the lymphatic system in addition to stimulating skeletal muscle or producing other biophysical or biochemical effects. As stated above, while the present embodiments of the invention focus on dominant low frequencies in the 1.5 Hz to 2.5 Hz range and particularly wave shapes comprising pulses separated by rests, the broadest aspect of the invention is the realisation that mobilisation of lymph using electrical stimulation is unexpectedly effective in healing ulcers, which has not been suggested by previous published investigations into the use of electrical currents in healing ulcers and has not been explored. Accordingly, other waveforms that are found in the future or have been previously identified (if any) to stimulate the lymphatic system are also within the scope of the current invention.

It is to be understood that, if any prior art publication is referred to herein, such reference does not constitute an admission that the publication forms a part of the common general knowledge in the art, in Australia or any other country.

BIBLIOGRAPHY

[Gault 1976] Gault W R, Gatens P F Jr; *Use of low intensity direct current in management of ischemic skin ulcers;* 1. Phys Ther. 1976 Mar; 56(3):265-9.

[Kloth 1988] L. C. Kloth et al; *Acceleration of wound healing with high voltage, monophasic, pulsed current;* Phys Ther. 1988; 68:503-5.

[Griffin 1991] J. W. Griffin et al; *Efficacy of high voltage pulsed current for healing of pressure ulcers in patients with spinal cord injury;* PHYS THER. 1991; 71:433-442.

[Feedar 1991] J. A. Feedar et. al.; *Chronic Dermal Ulcer Healing Enhanced With Monophasic Pulsed Electrical Stimulation;* Phys Ther. 1991; 71:639-649.

[Wood 1993] J. M. Wood et al; *A Multicentre Study On The Use Of Pulsed Low Intensity Direct Current For Healing*

*Chronic Stage II And Stage III Decubitus Ulcers;* Arch Dermatol 1993; Vol 129:999

[Baker 1996] L. L. Baker et al *Effect of electrical stimulation waveform on healing of ulcers in human beings with spinal cord injury;* Wound Rep Reg 1996; 4 :21-8

[Houghton 2003]; P. E. Houghton et al; *Effect Of Electrical Stimulation On Leg Ulcer Size;* Phys Ther. 2003; 83:17-28.

[Balakatounis 2008] K. C. Balakatounis and A. G. Angoules; *Low-intensity Electrical Stimulation in Wound Healing: Review of the Efficacy of Externally Applied Currents Resembling the Current of Injury;* eplasty Vol 8, 2008

[Piller 2010] N. Piller et al, *Placebo Controlled Trial Of Mild Electrical Stimulation;* four recommended four times daily 20 *minute treatment sessions Journal of Lymphoedema,* 2010, Vol 5, No 1:15-35

[Franek 2011] A. Franek et. al; *Effect Of High-Voltage Monophasic Electrical Stimulation On Pressure Leg Ulcers;* Wounds. 2011; 23(1):15-23.

[Doucet 2012] B. M. Doucet, A. Lam, and L. Griffin; *Neuromuscular Electrical Stimulation For Skeletal Muscle Function;* YALE Journal Of Biology And Medicine 85 (2012), pp. 201-215

[Walsh 2013] protocol for randomised control trial—*surface neuromuscular electrical stimulation in the treatment of chronic venous leg ulcers.* Clinicaltrials.gov

The invention claimed is:

1. A method comprising the step of using an electrical stimulation device for the treatment of a chronic venous ulcer on a leg of a patient, the method further comprising the steps of:
   providing an electrical stimulation device comprising one or more pairs of electrodes;
   positioning the one or more pairs of electrodes on the leg of the patient;
   connecting the electrical stimulation device to the one or more pairs of electrodes;
   configuring electrical stimulation produced by the electrical stimulation device to one having a time profile of pulses of current having a pulse width less than 12 ms and an interval between the pulses greater than 400 ms and less than 700 ms; and
   administering to the leg of the patient the electric stimulation through the one or more pairs of electrodes using the electric stimulation device in multiple treatment sessions until the chronic venous ulcer is reduced in size.

2. The method of claim 1 further comprising the step of limiting an instantaneous maximum current delivered during the pulses to less than 200 mA.

3. The method of claim 1 further comprising the step of arranging the pulses to comprise a first series of multiple pulses of a first polarity interspersed with a second series of multiple pulses of an opposite second polarity.

4. The method of claim 3, wherein there are less than 20 pulses in either of the series of pulses.

5. The method of claim 1, wherein most of the treatment sessions comprise a total period of administration of the stimulation of less than two hours and greater than 5 minutes.

6. The method of claim 1, wherein most of the treatment sessions comprise a total period of administration of the stimulation of about 20 minutes.

7. The method of claim 1, wherein there are at least two treatment sessions per week.

8. The method of claim 1, wherein the treatment sessions are continued after healing of the chronic venous ulcer so as to prevent recurrence of the chronic venous ulcer.

9. The method of claim 1 wherein the step of positioning the one or more pairs of electrodes comprises positioning to stimulate the lymphatic system proximate the chronic venous ulcer.

10. The method of claim 1, wherein the step of positioning the one or more pairs of electrodes comprises positioning to stimulate the lymphatic system along a substantial portion of the leg.

\* \* \* \* \*